(12) United States Patent
Das et al.

(10) Patent No.: US 10,283,275 B2
(45) Date of Patent: May 7, 2019

(54) FEEDTHROUGH SEAL APPARATUS, SYSTEM, AND METHOD

(71) Applicant: Greatbatch Ltd., Clarence, NY (US)

(72) Inventors: Biswa P. Das, Tonawanda, NY (US); Rommy U. Huleis, Minneapolis, MN (US); Afsar Ali, Maple Grove, MN (US); Ashish Shah, East Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 59 days.

(21) Appl. No.: 15/475,209

(22) Filed: Mar. 31, 2017

(65) Prior Publication Data

US 2017/0338043 A1 Nov. 23, 2017

Related U.S. Application Data

(60) Provisional application No. 62/339,130, filed on May 20, 2016.

(51) Int. Cl.
| | |
|---|---|
| *H01G 4/35* | (2006.01) |
| *A61N 1/375* | (2006.01) |
| *H02G 3/22* | (2006.01) |
| *H01G 9/10* | (2006.01) |
| *H01G 2/10* | (2006.01) |

(52) U.S. Cl.
CPC ............. *H01G 4/35* (2013.01); *A61N 1/3754* (2013.01); *H01G 2/103* (2013.01); *H01G 9/10* (2013.01); *H02G 3/22* (2013.01)

(58) Field of Classification Search
CPC ....................................................... H01G 4/35
USPC ........................................................ 174/667
See application file for complete search history.

(56) References Cited

U.S. PATENT DOCUMENTS

| | | | |
|---|---|---|---|
| 2,636,073 A | 4/1953 | Clarke et al. | |
| 2,873,304 A | 2/1959 | Davidson et al. | |
| 2,889,501 A | 6/1959 | Wilkens et al. | |
| 2,940,161 A | 6/1960 | Elarde et al. | |
| 3,237,060 A | 2/1966 | Ross et al. | |

(Continued)

FOREIGN PATENT DOCUMENTS

| | | |
|---|---|---|
| EP | 541530 A1 | 5/1993 |
| EP | 0870517 | 10/1998 |

(Continued)

OTHER PUBLICATIONS

Extended European Search Report, Application No. 17166880.9, dated Jun. 21, 2017.

*Primary Examiner* — Stanley Tso
(74) *Attorney, Agent, or Firm* — Michael P. Horvath

(57) ABSTRACT

In various examples, a feedthrough seal apparatus is configured to seal an opening in a device. The device includes a case surrounding an interior space, the case including the opening therein to allow access to the interior space from an exterior of the case. The feedthrough seal apparatus includes a plug disposed within the opening of the case. The plug is formed from at least one of a polymeric material and an adhesive material. The lead wire extends through the plug, such that a first end of the lead wire is disposed within the interior space of the case and a second end extends from the plug to the exterior of the case. The plug is configured to electrically insulate the lead wire from the case. Some examples include a method of making the feedthrough seal apparatus.

20 Claims, 11 Drawing Sheets

(56) References Cited

U.S. PATENT DOCUMENTS

| | | | |
|---|---|---|---|
| 3,264,708 A | 8/1966 | Diggens et al. | |
| 3,336,513 A | 8/1967 | Roy et al. | |
| 3,341,752 A | 9/1967 | Fournier et al. | |
| 3,483,449 A | 12/1969 | Natalis et al. | |
| 3,624,460 A | 11/1971 | Correll et al. | |
| 3,686,536 A | 8/1972 | Pearce et al. | |
| 3,874,929 A | 4/1975 | Greatbatch | |
| 3,956,819 A | 5/1976 | Augeri et al. | |
| 4,004,199 A | 1/1977 | Pearce et al. | |
| 4,037,142 A | 7/1977 | Poole et al. | |
| 4,166,158 A | 8/1979 | Rudolph et al. | |
| 4,168,351 A | 9/1979 | Taylor | |
| 4,479,168 A | 10/1984 | Green et al. | |
| 4,697,224 A | 9/1987 | Maesaka et al. | |
| 4,861,331 A | 8/1989 | Heindl et al. | |
| 5,766,042 A | 6/1998 | Ries et al. | |
| 5,811,206 A | 9/1998 | Sunderland et al. | |
| 5,905,627 A | 5/1999 | Brendel et al. | |
| 5,926,362 A | 7/1999 | Muffoletto et al. | |
| 5,944,660 A * | 8/1999 | Kimball | G01N 33/4925 356/246 |
| 6,061,710 A | 5/2000 | Eickemeyer et al. | |
| 6,159,560 A | 12/2000 | Stevenson et al. | |
| 6,248,080 B1 | 6/2001 | Miesel et al. | |
| 6,349,025 B1 * | 2/2002 | Fraley | A61N 1/3754 361/302 |
| 6,366,447 B1 | 4/2002 | Nakaaki et al. | |
| 6,409,776 B1 | 6/2002 | Untereker et al. | |
| 6,453,551 B1 | 9/2002 | Nordquist et al. | |
| 6,560,089 B2 | 5/2003 | Breyen et al. | |
| 6,795,729 B1 | 9/2004 | Breyen et al. | |
| 6,850,405 B1 | 2/2005 | Stemen et al. | |
| 6,898,822 B2 | 5/2005 | Nordquist et al. | |
| 7,092,242 B1 | 8/2006 | Gloss et al. | |
| 7,136,273 B2 | 11/2006 | Stevenson et al. | |
| 7,206,186 B1 | 4/2007 | Knight et al. | |
| 7,274,551 B1 | 9/2007 | Parler et al. | |
| 7,327,553 B2 | 2/2008 | Brendel | |
| 7,408,762 B2 | 8/2008 | Taller et al. | |
| 7,695,859 B2 | 4/2010 | Nielsen et al. | |
| 8,200,328 B2 | 6/2012 | Dabney et al. | |
| 8,213,160 B2 | 7/2012 | Takahashi et al. | |
| 8,259,435 B2 | 9/2012 | Galvagni et al. | |
| 8,451,586 B2 | 5/2013 | Priban et al. | |
| 2002/0071240 A1 | 6/2002 | Rorvick et al. | |
| 2002/0099430 A1 | 7/2002 | Verness et al. | |
| 2002/0115343 A1 | 8/2002 | Sommer et al. | |
| 2003/0056350 A1 | 3/2003 | Yan et al. | |
| 2003/0199941 A1 | 10/2003 | Nielsen et al. | |
| 2003/0199942 A1 | 10/2003 | Nielsen et al. | |
| 2004/0023109 A1 | 2/2004 | Rusin et al. | |
| 2004/0062985 A1 | 4/2004 | Aamodt et al. | |
| 2004/0062986 A1 | 4/2004 | Aamodt et al. | |
| 2004/0147974 A1 | 7/2004 | Engmark et al. | |
| 2004/0260354 A1 | 12/2004 | Nielsen et al. | |
| 2005/0131481 A1 | 6/2005 | Ries et al. | |
| 2005/0162810 A1 | 7/2005 | Seitz et al. | |
| 2005/0190527 A1 | 9/2005 | Stevenson et al. | |
| 2005/0213284 A1 | 9/2005 | Tatezono et al. | |
| 2005/0245983 A1 | 11/2005 | Kast et al. | |
| 2005/0247475 A1 | 11/2005 | Stevenson et al. | |
| 2006/0018079 A1 | 1/2006 | Barr et al. | |
| 2007/0060969 A1 | 3/2007 | Burdon et al. | |
| 2007/0182364 A1 * | 8/2007 | Zhao | A61N 1/375 320/107 |
| 2007/0234540 A1 * | 10/2007 | Iyer | H01G 2/106 29/25.42 |
| 2007/0253673 A1 | 11/2007 | Nielsen et al. | |
| 2008/0243200 A1 | 10/2008 | Scinicariello et al. | |
| 2008/0273287 A1 | 11/2008 | Marinkov et al. | |
| 2008/0292958 A1 | 11/2008 | Nielsen et al. | |
| 2008/0307621 A1 | 12/2008 | Schmidt et al. | |
| 2009/0059468 A1 | 3/2009 | Iyer | |
| 2009/0079518 A1 | 3/2009 | Iyer | |
| 2009/0079519 A1 | 3/2009 | Iyer | |
| 2009/0128987 A1 | 5/2009 | Zhao et al. | |
| 2009/0163981 A1 | 6/2009 | Stevenson et al. | |
| 2010/0134951 A1 | 6/2010 | Brendel et al. | |
| 2010/0202096 A1 | 8/2010 | Iyer et al. | |
| 2010/0284124 A1 | 11/2010 | Iyer et al. | |
| 2010/0284133 A1 * | 11/2010 | Skryten | H02G 3/22 361/679.01 |
| 2012/0106030 A1 | 5/2012 | Millman et al. | |
| 2013/0035732 A1 | 2/2013 | Miltich et al. | |
| 2013/0058003 A1 | 3/2013 | Iyer et al. | |
| 2013/0184796 A1 * | 7/2013 | Marzano | A61N 1/3754 607/116 |
| 2013/0325086 A1 | 12/2013 | Sommer et al. | |
| 2014/0167757 A1 | 6/2014 | Laskaris et al. | |
| 2014/0268498 A1 | 9/2014 | Weaver et al. | |

FOREIGN PATENT DOCUMENTS

| | | |
|---|---|---|
| EP | 2111256 B1 | 3/2014 |
| EP | 3163593 A1 | 5/2017 |
| EP | 3166117 A1 | 5/2017 |
| EP | 3171378 A1 | 5/2017 |
| GB | 700142 | 11/1953 |
| GB | 941139 A | 11/1963 |
| GB | 1015695 A | 1/1966 |
| GB | 1514872 A | 6/1978 |

* cited by examiner

FEEDTHROUGH SEAL APPARATUS, SYSTEM, AND METHOD

CROSS REFERENCE TO RELATED APPLICATIONS

This application claims the benefit of priority to U.S. Provisional Application Ser. No. 62/339,130, filed on May 20, 2016, entitled "FEEDTHROUGH SEAL APPARATUS, SYSTEM, AND METHOD," which is incorporated by reference herein in its entirety.

BACKGROUND

The present invention relates to a feedthrough seal apparatus, system, and, method, and more specifically relates to a capacitor feedthrough seal apparatus, system, and method.

In some instances, high voltage capacitors are used for implantable medical device applications. Capacitors paired with batteries can provide high-energy power solutions for various devices, such as, for instance, tachycardia devices. In some instances, the energy is delivered in the form of electrical current by a lead wire that originates at the anode in the capacitor and reaches out of the capacitor into the device. For the proper transfer of energy a seal is needed through which the lead wire can reach to the outside of the component. There are two primary functions of the seal: (1) to inhibit electrical conduction between the case and the wire; and (2) to inhibit material transfer from inside the capacitor into the device.

Typically, a feedthrough seal includes glass, which is melted and solidified between the inside of a ferrule and a concentrically placed tantalum wire. Such an assembly is known as a glass-to-metal seal (GTMS). The GTMS is prepared separately around the tantalum wire. A second tantalum wire from a formed anode assembly is cut to size, bead blasted to remove oxide layer, and then welded onto the tantalum wire coming from the GTMS. The anode and GTMS assembly then undergo a reforming step by heating. The ferrule of the GTMS is then laser welded to the capacitor case. Thus, the entire sealing procedure involves a number of steps making it a complex, expensive, and time-consuming process.

DETAILED DESCRIPTION

Figure 1:
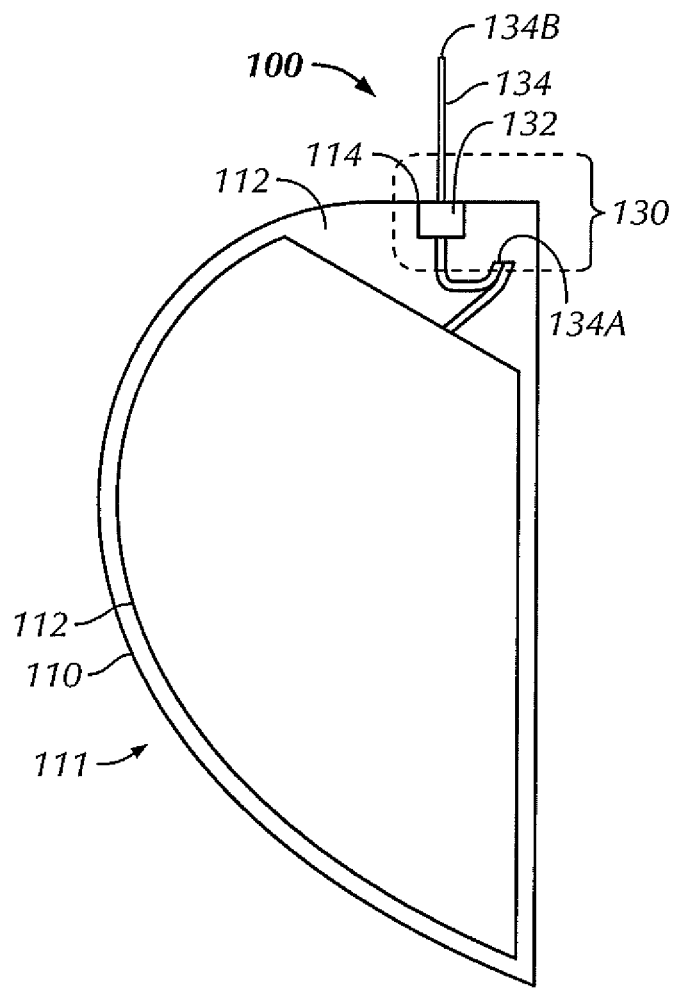
FIG. 1 is a cross-sectional view of a device including a feedthrough seal apparatus in accordance with at least one example of the invention.

The present subject matter relates to a feedthrough seal system, apparatus, and method. In some examples, the feedthrough seal system, apparatus, and method of the present patent application can be used for a feedthrough seal of a component, such as, for instance, a capacitor. The present subject matter can be used for a feedthrough seal for a component of a medical device in such a way as to reduce overall cost compared to current manufacturing methods.

The present inventors have recognized, among other things, that the present subject matter can be used for a feedthrough seal of a component of a medical device. In some examples, the present inventors have recognized that the present subject matter can be used to produce seals that are substantially functionally equivalent to, relatively simpler to manufacture than, and relatively less expensive than GTMS. For instance, compared to current seals (such as GTMS, for instance), the present subject matter, in various examples, can reduce manufacturing time, manufacturing difficulty, and material cost while achieving a seal that can withstand voltages of the component, inhibit current leakages between the wire and case, physically inhibit the wire and case from contacting one another, and inhibit movement of electrolyte molecules outside of the component.

In various examples, the feedthrough seal apparatuses described herein are configured to meet various performance and property requirements. Such requirements can include one or more of the following:

(1) The seal should be non-conductive;

(2) The seal should withstand a maximum charge voltage in the capacitor (for instance, in some examples, 420 V);

(3) The hermeticity should meet the standards followed by the industry (for instance, in some examples, leak rate should be less than $1 \times 10^{-7}$ std cc/sec, when tested in accordance with MIL-STD 883 Method 1014, Test conditions A2);

(4) The seal should be resistant to cleaning solvents, as well as the electrolyte; and (5) The seal should withstand mechanical tests undergone by the capacitor.

In some examples, the feedthrough seal apparatuses described herein are hermetic in that the feedthrough seal apparatuses are configured to meet a helium leak test with $1 \times 10^{-8}$ atm. cc/s being the threshold for pass or fail. In some examples, the feedthrough seal apparatuses described herein are configured to meet a helium leak test for hermeticity for a device feedthrough, in which $1 \times 10^{-9}$ atm. cc/s is the threshold for pass or fail.

In some examples, the feedthrough seal apparatuses can include one or more polymeric materials, including polysulfones, polyetherketones, and polyolefins such as polyethylene and polypropylene. In some examples, the polymeric materials can be in the unfilled form. In other examples, the polymeric materials can be in the filled form, incorporating one or more fillers, such as glass, ceramic, or clay particles or a combination thereof. In some examples, the feedthrough seal apparatuses include one or more bonding agents or adhesives, such as, but not limited to epoxy. In various examples, the feedthrough seal apparatuses can include one or more epoxies including, but not limited to, Loctite 3984 epoxy, Masterbond EP3HTMed epoxy, Cyberpoxy 5895 epoxy, and/or Epo-Tek 353ND epoxy.

Referring to FIG. 1, a component 100 of a device is shown. In some examples, the component 100 is a capacitor 100. In other examples, the component 100 can be a component other than a capacitor, such as, but not limited to, a battery. In some examples, the device within which the component 100 is disposed is a medical device. In further examples, the device is an implantable medical device. In other examples, the component 100 can be disposed within a device other than a medical device. For the sake of simplifying description, the examples herein refer to the component 100 as a capacitor 100; however, it should be understood that the component 100 is not limited to a capacitor 100 and can include any component, such as a battery, for instance.

In some examples, the capacitor 100 includes a case 110 surrounding an interior space 112 of the capacitor. In some examples, the case 110 can be formed from a metallic material, such as, but not limited to titanium, stainless steel, or the like. In some examples, the case 110 includes an opening 114 therein to allow access to the interior space 112 from an exterior 111 of the case 110. In some examples, the capacitor 100 includes an anode 120 and an electrolyte material within the interior space 112 of the case 110.

In some examples, the capacitor 100 includes a feedthrough seal apparatus 130 in order to fluidly seal the opening 114 of the case 110 while still allowing electrical communication between the exterior 111 and the interior space 112 of the case 110 but electrically insulating the interior space 112 from the exterior 111 of the case 110. In various examples, the feedthrough seal apparatus 130 aids in inhibiting electrolyte material (and other materials) from escaping from the interior space 112 and outside materials and/or contaminants from entering the interior space 112 of the case 110. In some examples, the feedthrough seal apparatus 130 includes a plug 132 disposed within the opening 114 of the case 110 and a lead wire 134 extending through the plug 132. In various examples, some of which are described below, the plug 132 can be formed from various materials, including one or more polymeric materials, one or more adhesive materials, one or more glass materials, and one or more ceramic materials or various combinations thereof. The plug 132, in some examples, is configured to be electrically insulative, among other things. In this way, in some examples, the plug 132 is configured to insulate the interior space 112 of the case 110 and the contents thereof from the exterior 111 of the case 110. In further examples, the plug 132 is configured to electrically insulate the lead wire 134 from the case 110 and/or other components of the capacitor 100 and/or device.

In some examples, the lead wire 134 includes a first end 134A and a second end 134B. In some examples, the lead wire 134 extends through the plug 132, such that the first end 134A of the lead wire 134 is disposed within the interior space 112 of the case 110 and the second end 134B extends from the plug 132 to the exterior 111 of the case 110. In some examples, the first end 134A of the lead wire 134 is configured to electrically couple to the anode 120. In further examples, the second end 134B of the lead wire 134 is configured to electrically couple to circuitry within the device but outside of the case 110 of the capacitor 100. In various examples, the lead wire 134 is configured to allow electrical communication between the interior space 112 of the case 110 (and/or one or more components therein) and the exterior 111 of the case 110. In some examples, the lead wire 134 is formed from a metallic material, such as, but not limited to, tantalum. In this way, in some examples, the feedthrough seal apparatus 130 is configured to seal the opening 114 in the case 110. In some examples, the feedthrough seal apparatus 130 is configured to hermetically seal the opening 114 in the case 110.

Figure 2A:
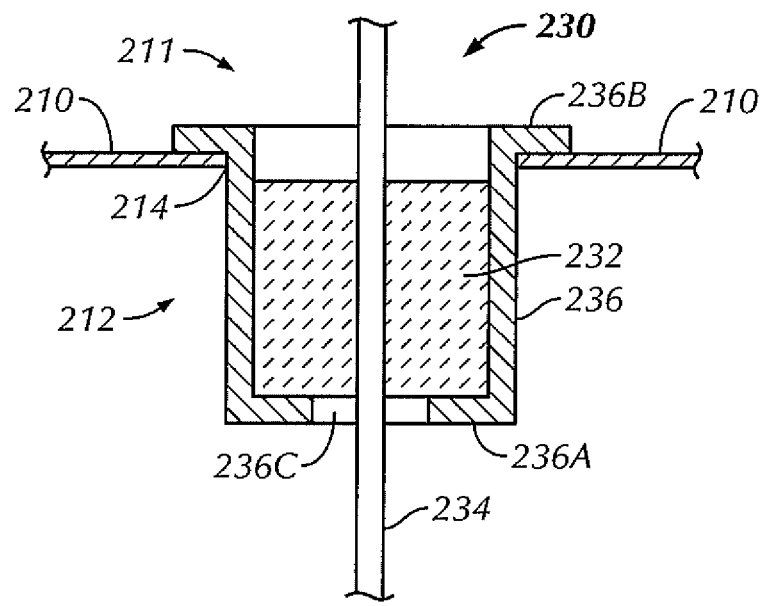
FIG. 2A is a cross-sectional view of a feedthrough seal apparatus in accordance with at least one example of the invention.
Figure 2B:
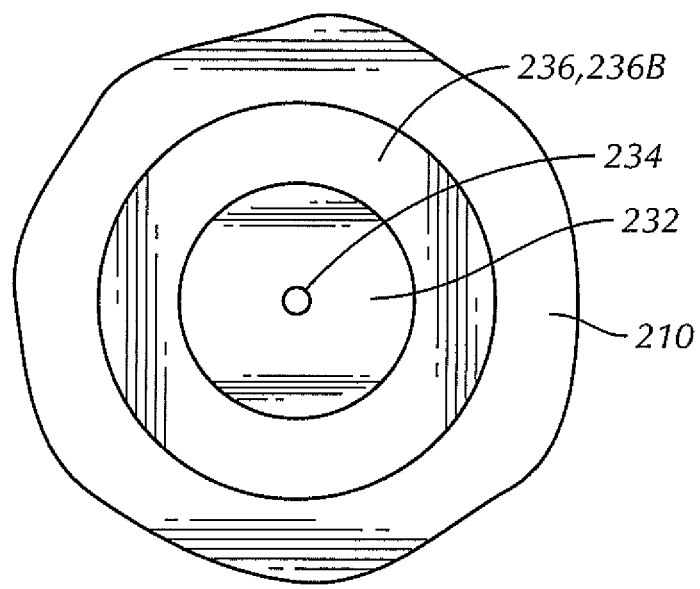
FIG. 2B is a top view of a feedthrough seal apparatus in accordance with at least one example of the invention.

Referring to FIGS. 2A and 2B, in some examples, a feedthrough seal apparatus 230 can be used within a device, such as a medical device. In further examples, the feedthrough seal apparatus 230 can be used in a component of the device, such as the capacitor 100 described above. In some examples, the feedthrough seal apparatus 230 is configured to seal an opening 214 in a case 210. In some examples, the feedthrough seal apparatus 230 includes a lead wire 234 disposed within a plug 232 for sealing the opening 214 of the case 210 while, at the same time, allowing electrical communication (through the lead wire 234) between an interior space 212 of the case 210 and an exterior 211 of the case 210.

In some examples, the feedthrough seal apparatus 230 includes a ferrule 236. In some examples, the ferrule 236 is formed, at least in part, from a metallic material. The ferrule 236, in some examples, can be disposed within the opening 214 of the case 210 and attached to the case 210. In some examples, the ferrule 236 includes a flange 236B or other structure to facilitate attachment to the case 210. In some examples, the flange 236B is welded to the case 210. In some examples, other ways of attachment are used, such as press-fitting, adhesive, or the like. Although shown with a flange 236B in FIGS. 2A and 2B, it should be understood that the ferrule 236 does not require the flange 236B in order to be attached to the case 210 and can be welded, press-fit, adhered, or otherwise attached to the case 210 even without the flange 236B. In some examples, the ferrule 236 is substantially cylindrical in shape such that the ferrule is substantially circular when viewed from an end (see FIG. 2B). However, in other examples, the ferrule can include other shapes when viewed from an end, such as, but not limited to ovular, elliptical, or polygonal. In various examples, the ferrule 236 is formed from a metallic material, such as, but not limited to, titanium, stainless steel, or the like.

In some examples, the plug 232 is disposed within the ferrule 236. In some examples, the plug 232 is affixed within and/or to the ferrule 236. In further examples, the plug 232 is affixed to the lead wire 234, in addition to or instead of the ferrule 236. In some examples, the plug 232 includes a polymeric material, which can be affixed to the ferrule 236 and/or the lead wire 234 using an adhesive. In further examples, the plug 232 includes a thermoplastic polymeric material, which can be thermally joined to the ferrule 236 and/or the lead wire 234 with heating of the thermoplastic polymeric material. In some examples, the plug 232 can be bulk heated (in an oven, for instance), which causes the entire plug 232 to heat up, thereby allowing the plug 232 to become at least partially flowable to adhere the plug 232 to the ferrule 236 and/or the lead wire 234. In other examples, the plug 232 can be locally heated (for instance, using laser or electrical energy) to heat portions of the plug 232 abutting the ferrule 236 and/or the lead wire 234, thereby allowing portions of the plug 232 abutting the ferrule 236 and/or the lead wire 234 to become at least partially flowable to adhere the plug 232 to the ferrule 236 and/or the lead wire 234. In some examples, the plug 232 can include a polymeric material that is sized and shaped to correspond to an interior of the ferrule 236, such that the plug 232 can be press-fit into the ferrule 236 to affix the plug 232 at least partially within the ferrule 236. In some examples, the plug 232 can include a passage therethough sized and shaped to allow sealing, press-fit engagement with the lead wire 234.

In some examples, the plug 232 is formed from an adhesive, such that the adhesive, in a flowable state, can be poured, injected, or otherwise placed within the ferrule 236 to solidify, cure, or otherwise harden, thereby taking the shape of the interior of the ferrule 236. In this way, the adhesive forms the plug 232 and adheres the plug 232 to the ferrule 236 and/or the lead wire 234. In some examples, the plug 232 is formed from epoxy.

In some examples, the ferrule 236 includes an inwardly-extending portion 236A. In some examples, the inwardly-extending portion 236A reduces the size of a ferrule opening 236C than would otherwise be present if there were no inwardly-extending portion. In some examples, the inwardly-extending portion 236A is disposed at an end of the ferrule 236. In other examples, the inwardly-extending portion can be disposed at a location intermediate ends of the ferrule.

In some examples, with the plug 232 formed from an adhesive, the inwardly-extending portion 236A decreases the size of the ferrule opening 236C, and, in turn, aids in retaining the adhesive within the ferrule 236 after insertion of the adhesive into the ferrule 236 and before the adhesive solidifies, cures, or otherwise hardens. That is, the decreased size of the ferrule opening 236C lessens the likelihood of adhesive escaping or otherwise leaking through the ferrule opening 236C. Additionally, in some examples, viscosity of the adhesive can also aid in retaining the adhesive within the ferrule 236 after insertion of the adhesive into the ferrule 236 and before the adhesive solidifies, cures, or otherwise hardens. The more viscous the adhesive, the less likely it is that the adhesive escapes or otherwise leaks through the ferrule opening 236C. However, it is noted that the more viscous the adhesive, the less easily it will flow and fill up the ferrule 236. Therefore, in some examples, a viscosity of the adhesive can be achieved such that the adhesive will flow into the ferrule 236 but not leak through the ferrule opening 236C.

In some examples, with the plug 232 formed from a polymeric material, the inwardly-extending portion 236A provides for a surface on which the plug 232 can rest to facilitate proper placement within the ferrule 236 and/or inhibit migration of the plug 236 outside of the ferrule 236 and toward the interior space 212 of the case 210. For instance, in some examples, the plug 232 can rest on the inwardly-extending portion 236A during affixation of the plug 232 to the ferrule 236 and/or the lead wire 234, thereby maintaining the plug 232 in position within the ferrule 236 during thermal joining, application and curing of adhesive, or other affixation techniques.

Figure 3A:
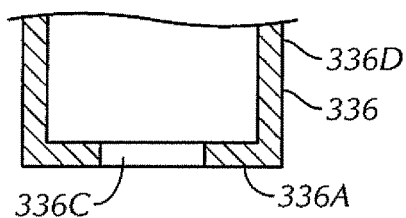
FIGS. 3A and 3B are cross-sectional views of a ferrule of a feedthrough seal apparatus in accordance with at least one example of the invention.
Figure 3B:
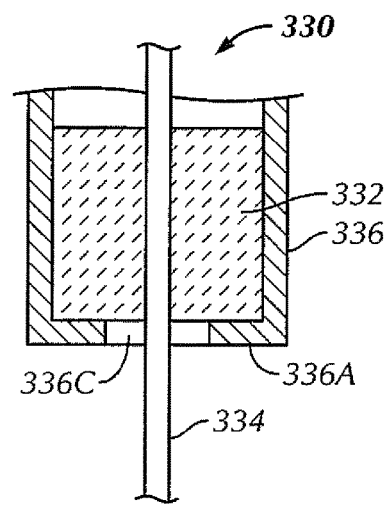

Referring to FIGS. 3A and 3B, in some examples, a feedthrough seal apparatus 330 includes a ferrule 336 that includes an inwardly-extending portion 336A, which decreases the size of a ferrule opening 336C (for instance, the space between the ferrule 336 and a lead wire 334). In some examples, the inwardly-extending portion 336A includes a stepped feature 336A. In some examples, the stepped feature 336A extends inwardly from a sidewall 336D of the ferrule 336 at an angle of substantially ninety degrees with respect to the sidewall 336D. In other examples, the stepped feature 336A can extend from the sidewall 336D at angles other than substantially ninety degrees, such as, for instance, less than ninety degrees, such that the stepped feature 336A extends in an inward and upward direction (with respect to FIGS. 3A and 3B) within an interior of the ferrule 336. In various examples, the stepped feature 336A can provide for a surface on which a plug 332 can rest to facilitate proper placement within the ferrule 336 and/or inhibit migration of the plug 336 outside of the ferrule 336 and toward the interior space of the case and/or can aid in retaining the plug 332 (if formed from an adhesive) within the ferrule 336 after insertion of the adhesive into the ferrule 336 and before the adhesive solidifies, cures, or otherwise hardens due to the decreased size of the ferrule opening 336C.

Figure 4A:
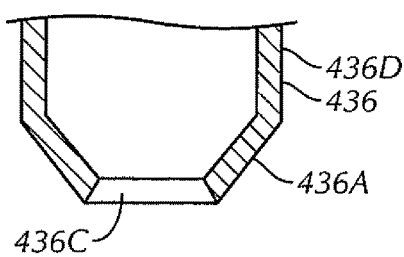
FIGS. 4A and 4B are cross-sectional views of a ferrule of a feedthrough seal apparatus in accordance with at least one example of the invention.
Figure 4B:
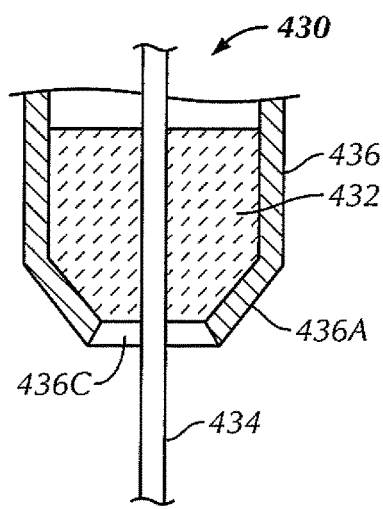

Referring to FIGS. 4A and 4B, in some examples, a feedthrough seal apparatus 430 includes a ferrule 436 that includes an inwardly-extending portion 436A, which decreases the size of a ferrule opening 436C (for instance, the space between the ferrule 436 and a lead wire 434). In some examples, the inwardly-extending portion 436A includes a tapered feature 436A. In some examples, the tapered feature 436A extends inwardly from a sidewall 436D of the ferrule 436 at an angle of greater than ninety degrees with respect to the sidewall 436D, such that the tapered feature 436A extends in an inward and downward direction (with respect to FIGS. 4A and 4B) from the sidewall 436D of the ferrule 436. In various examples, the tapered feature 436A can provide for a surface on which a plug 432 can rest to facilitate proper placement within the ferrule 436 and/or inhibit migration of the plug 436 outside of the ferrule 436 and toward the interior space of the case and/or can aid in retaining the plug 432 (if formed from an adhesive) within the ferrule 436 after insertion of the adhesive into the ferrule 436 and before the adhesive solidifies, cures, or otherwise hardens due to the decreased size of the ferrule opening 436C.

Figure 5:
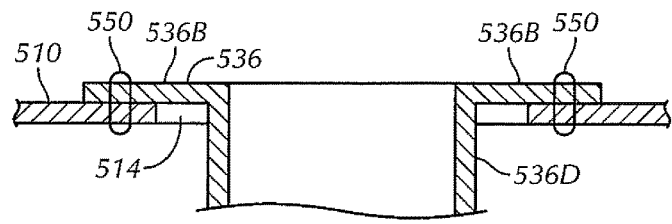
FIG. 5 is a cross-sectional view of a ferrule of a feedthrough seal apparatus in accordance with at least one example of the invention.

Referring to FIG. 5, in some examples, a ferrule 536 can include a flange 536B that is longer than the flange 236B described above. The longer flange 536B, in some examples, allows for one or more welds 550 to be spaced at a greater distance from a sidewall 536D of the ferrule 536 than if the flange were shorter. In this way, welding the flange 536D to a case 510 can be accomplished with less risk of harming the lead wire, the plug, or any other component due to the heat generated during the welding process. For instance, in some examples, heat from welding can decompose adhesive used with respect to the plug, so keeping the location of the weld 550 at a greater distance from the adhesive allows for greater dissipation of heat within the ferrule 536 and lessens the chances of the heat decomposing, breaking down, or otherwise adversely affecting the plug and/or the adhesive.

Figure 6:
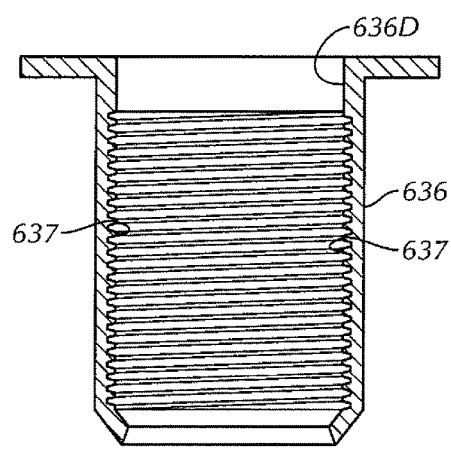
FIG. 6 is a cross-sectional view of a ferrule of a feedthrough seal apparatus in accordance with at least one example of the invention.

Referring to FIG. 6, in some examples, a ferrule 636 includes an adhesion feature 637 configured to enhance adhesion between the ferrule 636 and a plug. In some examples, an interior surface of a sidewall 636D of the ferrule 636 includes the adhesion feature 637, which includes one or more bumps, roughness, pegs, dimples, ridges, ribs, holes, pores, or the like or a combination thereof. In this way, the adhesion feature 637 is configured to increase surface area and provide texture to enhance affixation of the plug thereto and provide a mechanical bond between the plug and the ferrule 636, whether the plug is formed from an adhesive (such as, but not limited to, epoxy) inserted into the ferrule 636 and allowed to set, cure, or otherwise harden or a polymeric material which is heated to thermally join the plug to the ferrule 636 (using either bulk heating or local heating, for instance) or is affixed to the ferrule 636 using adhesive.

Figure 7:
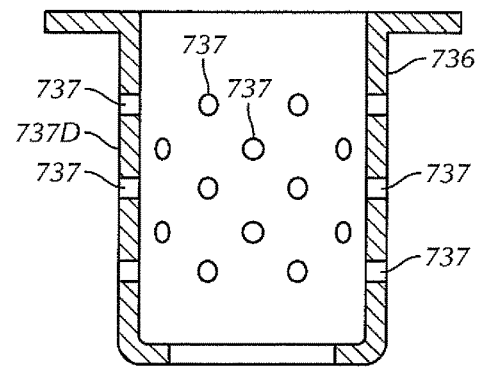
FIG. 7 is a cross-sectional view of a ferrule of a feedthrough seal apparatus in accordance with at least one example of the invention.

Referring to FIG. 7, in some examples, a ferrule 736 includes an adhesion feature 737 configured to enhance adhesion between the ferrule 736 and a plug. In some examples, a sidewall 736D of the ferrule 736 includes the adhesion feature 737, which includes one or more holes, pores, openings, channels, voids, or the like or a combination thereof through the sidewall 736D from an interior surface of the sidewall 736D to an exterior surface of the sidewall 736D. In this way, the adhesion feature 737 is configured to allow the plug to flow at least partially into the adhesion feature 737 to enhance affixation of the plug thereto and provide a mechanical bond between the plug and the ferrule 736, whether the plug is formed from an adhesive (such as, but not limited to, epoxy) inserted into the ferrule 736 and allowed to set, cure, or otherwise harden or a polymeric material which is heated to thermally join the plug to the ferrule 736 (using either bulk heating or local heating, for instance) or is affixed to the ferrule 736 using adhesive.

Figure 8:
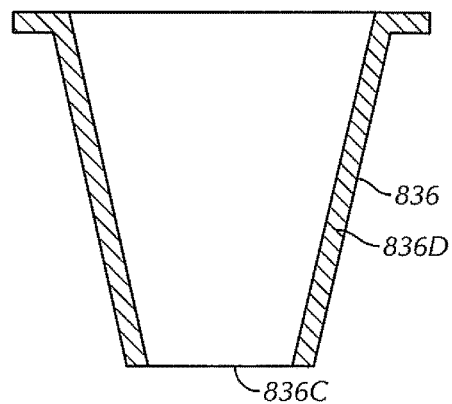
FIG. 8 is a cross-sectional view of a ferrule of a feedthrough seal apparatus in accordance with at least one example of the invention.

Referring to FIG. 8, in some examples, a ferrule 836 includes a non-cylindrical shape. In some examples, the ferrule 836 includes an angled sidewall 836D such that the ferrule 836 essentially forms a frustoconical shape. In this way, the angled sidewall 836D is similar to the inwardly-extending portion 436A of the example ferrule 436 shown in FIGS. 4A and 4B except that the angled sidewall 836D extends for substantially the entire length of the ferrule 836 and not just a portion of it. In this way, the shape of the ferrule 836 allows for a ferrule opening 836C to be decreased in size than if the ferrule were to include straight sidewalls and be more cylindrical in shape. In various examples, the angled sidewall 836D can provide for a surface on which a plug can rest to facilitate proper placement within the ferrule 836 and/or inhibit migration of the plug outside of the ferrule 836 and toward the interior space of the case and/or can aid in retaining the plug (if formed from an adhesive) within the ferrule 836 after insertion of the adhesive into the ferrule 836 and before the adhesive solidifies, cures, or otherwise hardens due to the decreased size of the ferrule opening 836C. Although the example ferrule 836 shown in FIG. 8 includes a substantially uniformly angled sidewall 836D, in other examples, other non-cylindrical ferrule shapes are contemplated, such as, for instance, a curved sidewall (inwardly curving to provide for a decreased ferrule opening), an angled sidewall having at least a first portion angled at a first angle (with respect to a longitudinal axis) and a second portion angled at a second angle (with respect to the longitudinal axis), a stepped sidewall, or one or more other substantially non-cylindrically-shaped sidewalls.

Figure 9:
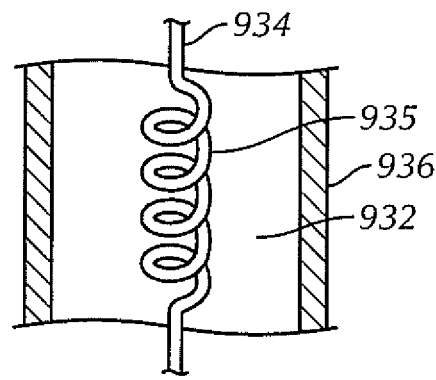
FIG. 9 is a cross-sectional view of a lead wire for a feedthrough seal apparatus in accordance with at least one example of the invention.
Figure 10:
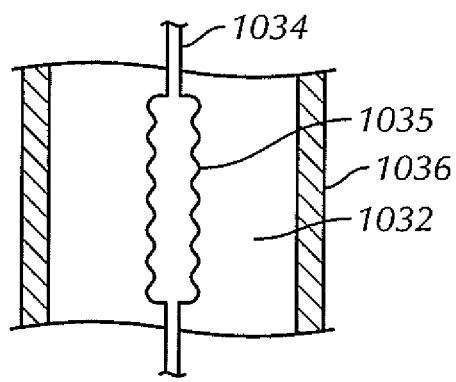
FIG. 10 is a cross-sectional view of a lead wire for a feedthrough seal apparatus in accordance with at least one example of the invention.
Figure 11:
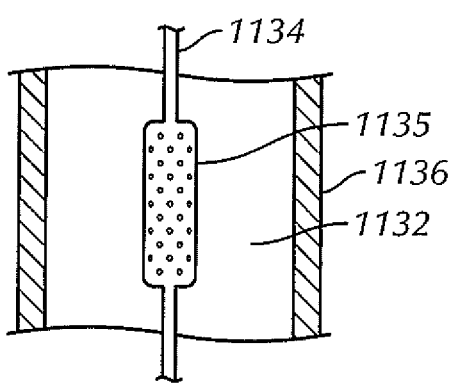
FIG. 11 is a cross-sectional view of a lead wire for a feedthrough seal apparatus in accordance with at least one example of the invention.

Referring to FIGS. 9-11, in some examples, a lead wire 934, 1034, 1134 can include an adhesion feature 935, 1035, 1135 configured to enhance adhesion between the lead wire 934, 1034, 1134 and a plug 932, 1032, 1132. In various examples, the adhesion feature 935, 1035, 1135 can include various structures or features to increase surface area and provide texture to enhance affixation of the lead wire 934, 1034, 1134 to the plug 932, 1032, 1132 and provide a mechanical bond between the plug 932, 1032, 1132 and the lead wire 934, 1034, 1134, whether the plug 932, 1032, 1132 is formed from an adhesive (such as, but not limited to, epoxy) inserted into a ferrule 936, 1036, 1136 and allowed to set, cure, or otherwise harden or a polymeric material which is heated to thermally join the plug 932, 1032, 1132 to the lead wire 934, 1034, 1134 or is affixed to the lead wire 934, 1034, 1134 using adhesive. In various examples, the adhesion feature 935, 1035, 1135 of the lead wire 934, 1034, 1134 can be used instead of or in addition to an adhesion feature of the ferrule 936, 1036, 1136 (such as an adhesion feature similar to the adhesion feature 637 described above, for instance). It is contemplated in various examples that various adhesion features 935, 1035, 1135 can be used with the lead wire 934, 1034, 1134, including, but not limited to, one or more bumps, roughness, pegs, dimples, ridges, ribs, or the like or a combination thereof.

For instance, with respect to FIG. 9, the adhesion feature 935 of the lead wire 934 includes a bent portion 935 of the lead wire 934. In some examples, the bent portion 935 can be substantially helical. In other examples, the bent portion 935 can include a substantially wavy portion, a substantially saw-tooth portion, or portions include various other bend patterns. In some examples, the lead wire 934 can include a bent portion including a single bend. In other examples, the lead wire 934 can include a bent portion including multiple bends. In some examples, the lead wire 934 can include a bent portion including two or more different bend patterns.

With respect to FIG. 10, the adhesion feature 1035 of the lead wire 1034 includes a textured surface 1035 of the lead wire 1034. In some examples, the textured surface 1035 of the lead wire 1034 includes bumps 1035 along a portion of the lead wire 1034 to provide increased surface area and/or texture around and within which adhesive or polymeric material of the plug 1032 forms to enhance affixation of the lead wire 1034 to the plug 1032. In other examples, the textured surface 1035 can include ridges, dimples, channels, or other patterns or textures or a combination of patterns or textures.

With respect to FIG. 11, the adhesion feature 1135 of the lead wire 1134 includes a porous surface 1135 of the lead wire 1134. In some examples, the porous surface 1135 of the lead wire 1134 includes holes 1135 along a portion of the lead wire 1134 to provide increased surface area and/or texture around and within which adhesive or polymeric material of the plug 1132 forms to enhance affixation of the lead wire 1134 to the plug 1132. In other examples, the porous surface 1135 can include dimples, channels, or other patterns or textures or a combination of patterns or textures.

Referring again to FIGS. 9-11, it is noted that in various examples, a lead wire can include a combination of two or more of the adhesion features 935, 1035, 1135. For instance, in some examples, a lead wire can include a bent portion 935 in combination with a porous surface 1135. In other examples, a lead wire can include a textured surface 1035 in combination with a porous surface 1135. In other examples, a lead wire can include a bent portion 935 in combination with a textured surface 1035. And, in further examples, a lead wire can include a bent portion 935 in combination with a textured surface 1035 and a porous surface 1135. In this way, affixation of the various lead wire examples with a plug is enhanced by increasing the surface area and/or texture around and/or within which adhesive or polymeric material of a plug interacts.

In various examples, referring still to FIGS. 9-11, the lead wire 934, 1034, 1134 can include various cross sections. In some examples, the lead wire 934, 1034, 1134 includes a substantially circular cross section. However, in other examples, the lead wire 934, 1034, 1134 can include a non-circular cross section, potentially providing for increased affixation between the lead wire 934, 1034, 1134 and the plug 932, 1032, 1132. For instance, in some examples, a non-circular cross section can inhibit twisting between the lead wire 934, 1034, 1134 and the plug 932, 1032, 1132. Some examples of non-circular cross sections that can be employed along at least a portion of the lead wire 934, 1034, 1134 include, but are not limited to, cross sections that are square, quadrilateral, triangular, ovular, elliptical, star-shaped, flat, polygonal, lobed, or the like. In some examples, the lead wire 934, 1034, 1134 can include two or more different cross-sectional shapes, such as the various cross-sectional shape examples above, over at least a portion of the length of the lead wire 934, 1034, 1134. One or more of such non-circular cross sections can be employed, in some examples, in addition to one or more of the adhesion features 935, 1035, 1135 described above, to further enhance affixation between the lead wire and the plug. However, in other examples, a lead wire can include one or more a non-circular cross sections along at least a portion of the length of the lead wire without employing one or more of the adhesion features 935, 1035, 1135 described above, depending upon the desired characteristics of adhesion and/or interaction between the lead wire and the plug.

Figure 12:
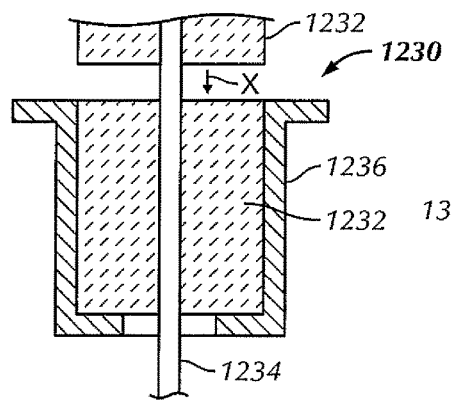
FIG. 12 is a cross-sectional view of a feedthrough seal apparatus in accordance with at least one example of the invention.

Referring to FIG. 12, in some examples, a feedthrough seal apparatus 1230 includes a ferrule 1236, the ferrule 1236 being attached within an opening of a case or other device or component, as described herein. In some examples, the feedthrough seal apparatus 1230 includes a lead wire 1234 extending from an interior of the case to an exterior of the case. In some examples, a plug 1232 can include a polymeric material and can be inserted into the ferrule 1236 by sliding it in the direction of arrow X along the lead wire 1234 and into the ferrule 1236. In some examples, the plug 1232 is sized and shaped to correspond to an interior of the ferrule 1236 to allow the plug 1232 to be press-fit into the ferrule 1236 to affix the plug 1232 at least partially within the ferrule 1236. In some examples, the plug 1232 is formed from a thermoplastic polymeric material and is sized and shaped to fit snugly within the ferrule 1236 and around the lead wire 1234, thereby allowing for heating (for instance, either bulk or local heating) of the plug 1232 to thermally join the plug 1232 to the ferrule 1236 and the lead wire 1234. In further examples, the plug 1232 can be designed to match an inner geometry of the ferrule 1236. In other examples, the plug 1232 is sized and shaped to allow for space between the plug 1232 and the ferrule 1236 and between the plug 1232 and the lead wire 1234 to allow for placement of adhesive within the space to affix the plug 1232 to the ferrule 1236 and the lead wire 1234. In some examples, one or both of the ferrule 1236 and the lead wire 1234 include an adhesion feature, as described herein.

Figure 13A:
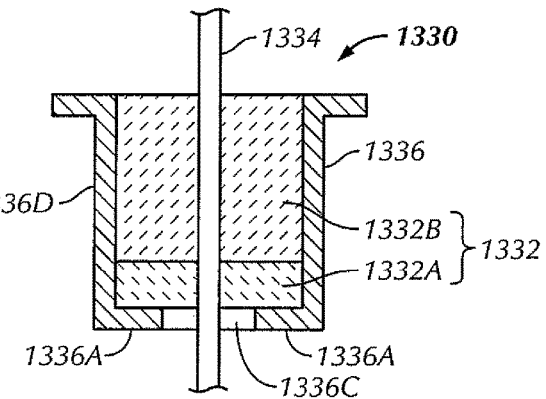
FIG. 13A is a cross-sectional view of a feedthrough seal apparatus in accordance with at least one example of the invention.
Figure 13B:
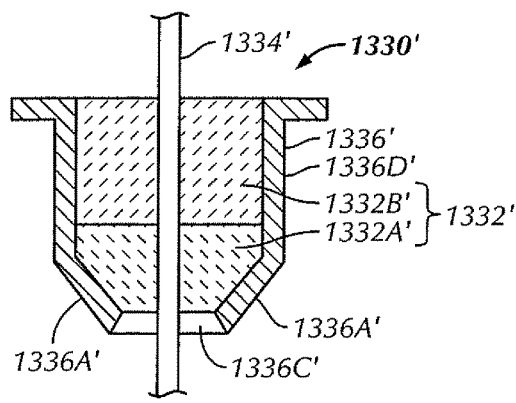
FIG. 13B is a cross-sectional view of a feedthrough seal apparatus in accordance with at least one example of the invention.
Figure 13C:
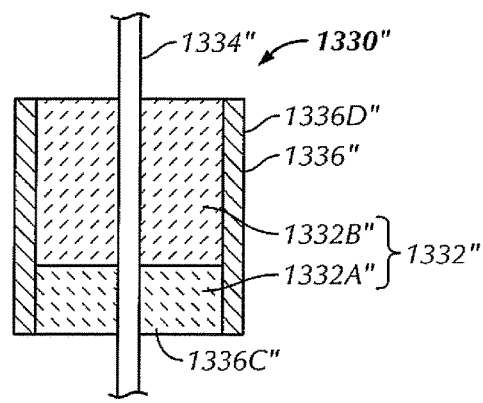
FIG. 13C is a cross-sectional view of a feedthrough seal apparatus in accordance with at least one example of the invention.

Referring to FIGS. 13A-13C, in some examples, a feedthrough seal apparatus 1330, 1330', 1330" includes a ferrule 1336, 1336', 1336", the ferrule 1336, 1336', 1336" being attached within an opening of a case or other device or component, as described herein. In some examples, the feedthrough seal apparatus 1330, 1330', 1330" includes a lead wire 1334, 1334', 1334" extending from an interior of the case to an exterior of the case. In some examples, one or both of the ferrule 1336, 1336', 1336" and the lead wire 1334, 1334', 1334" include an adhesion feature, as described herein. In some examples, a plug 1332, 1332', 1332" can include a polymeric portion 1332A, 1332A', 1332A" and an adhesive portion 1332B, 1332W, 1332B". In some examples, the polymeric portion 1332A, 1332A', 1332A" can be inserted into the ferrule 1336, 1336', 1336" by sliding it in the direction along the lead wire 1334, 1334', 1334" and into the ferrule 1336, 1336', 1336". In some examples, the polymeric portion 1332A, 1332A', 1332A" is sized and shaped to correspond to an interior of the ferrule 1336, 1336', 1336" to allow the polymeric portion 1332A, 1332A', 1332A" to be press-fit into the ferrule 1336, 1336', 1336" to affix the polymeric portion 1332A, 1332A', 1332A" at least partially within the ferrule 1336, 1336', 1336". In some examples, the polymeric portion 1332, 1332', 1332" is formed from a thermoplastic polymeric material and is sized and shaped to fit snugly within the ferrule 1336, 1336', 1336" and around the lead wire 1334, 1334', 1334", thereby allowing for heating (either bulk or local heating, for instance) of the polymeric portion 1332, 1332', 1332" to thermally join the polymeric portion 1332, 1332', 1332" to the ferrule 1336, 1336', 1336" and the lead wire 1334, 1334', 1334". In further examples, the plug 1332, 1332', 1332" can be designed to match an inner geometry of the ferrule 1336, 1336', 1336". In other examples, the polymeric portion 1332A, 1332A', 1332A" is sized and shaped to allow for space between the polymeric portion 1332A, 1332A', 1332A" and the ferrule 1336, 1336', 1336" and between the polymeric portion 1332A, 1332A', 1332A" and the lead wire 1334, 1334', 1334" to allow for placement of adhesive within the space to affix the polymeric portion 1332A, 1332A', 1332A" to the ferrule 1336, 1336', 1336" and the lead wire 1334, 1334', 1334". In some examples, the polymeric portion 1332A, 1332A', 1332A" can aid in positioning of the lead wire 1334, 1334', 1334" with respect to the ferrule 1336, 1336', 1336". In some examples, the polymeric portion 1332A, 1332A', 1332A" can help center the lead wire 1334, 1334', 1334" with respect to the ferrule 1336, 1336', 1336". That is, in some examples, formation of a hole within the polymeric portion 1332A, 1332A', 1332A" for the lead wire 1334, 1334', 1334" (for instance, substantially centered within the polymeric portion 1332A, 1332A', 1332A") with respect to an outer perimeter of the polymeric portion 1332A, 1332A', 1332A" can allow for proper spacing between the lead wire 1334, 1334', 1334" and the ferrule 1336, 1336', 1336", thereby making it less likely for the lead wire 1334, 1334', 1334" to come into contact with the ferrule 1336, 1336', 1336" once the plug 1332, 1332', 1332" is positioned within the ferrule 1336, 1336', 1336". Once the polymeric portion 1332A, 1332A', 1332A" is in position within the ferrule 1336, 1336', 1336", in some examples, adhesive can be inserted within the ferrule 1336, 1336', 1336" to form the adhesive portion 1332B, 1332B', 1332B" of the plug 1332, 1332', 1332" and fill at least a portion of the ferrule 1336, 1336', 1336" on top of the polymeric portion 1332A, 1332A', 1332A". In some examples, the use of the polymeric portion 1332A, 1332A', 1332A" aids in closing off a ferrule opening 1336C, 1336C', 1336C", such that adhesive with a lower viscosity can be used (as compared to an adhesive used without a polymeric portion and, in turn, a larger ferrule opening, as described above). That is, because the ferrule opening 1336C, 1336C', 1336C" is largely (if not completely) closed off by the polymeric portion 1332A, 1332A', 1332A", there is not as large of a gap to span with the adhesive (as there is in examples above), and, therefore, a less viscous adhesive would be less likely to leak from the ferrule opening 1336C, 1336C', 1336C" than if the ferrule opening 1336C, 1336C', 1336C" were not largely closed off by the polymeric portion 1332A, 1332A', 1332A".

In various examples, different configurations of the ferrule 1336, 1336', 1336" can be used. For instance, referring to FIG. 13A, in some examples, a sidewall 1336D of the ferrule 1336 includes an inwardly-extending portion 1336A. In some examples, the inwardly-extending portion 1336A reduces the size of the ferrule opening 1336C than would otherwise be present if there were no inwardly-extending portion. In some examples, the inwardly-extending portion 1336A is disposed at an end of the ferrule 1336. In other examples, the inwardly-extending portion can be disposed at a location intermediate ends of the ferrule. In some examples, the inwardly-extending portion 1336A can be configured to support the polymeric portion 1332A and retain the polymeric portion 1332A within the ferrule 1336. In this way, the polymeric portion 1332A is inhibited from passing through and/or out of the ferrule 1336.

Referring to FIG. 13B, in some examples, a sidewall 1336D' of the ferrule 1336' includes an inwardly-extending portion 1336A', which decreases the size of the ferrule opening 1336C' (for instance, the space between the ferrule 1336' and a lead wire 1334'). In some examples, the inwardly-extending portion 1336A' includes a tapered feature 1336A'. In some examples, the tapered feature 1336A' extends inwardly from the sidewall 1336D' of the ferrule 1336' at an angle of greater than ninety degrees with respect to the sidewall 1336D', such that the tapered feature 1336A' extends in an inward and downward direction (with respect to FIG. 13B) from the sidewall 1336D' of the ferrule 1336'. In some examples, the tapered feature 1336A' can be configured to support the polymeric portion 1332A' and retain the polymeric portion 1332A' within the ferrule 1336'. In this way, the polymeric portion 1332A' is inhibited from passing through and/or out of the ferrule 1336'.

Referring to FIG. 13C, in some examples, a sidewall 1336D" of the ferrule 1336" is substantially straight, such that the ferrule 1336" is substantially cylindrical in shape. In this way, in some examples, a frictional fit between the polymeric portion 1332A" and the ferrule 1336" and/or between the polymeric portion 1332A" and the lead wire 1334" is used to retain the polymeric portion 1332A" within the ferrule 1336" and inhibit the polymeric portion 1332A" from passing through and/or out of the ferrule 1336".

Figure 14A:
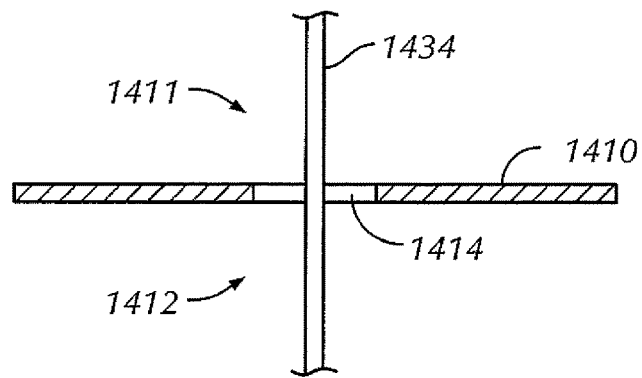
FIG. 14A is a cross-sectional view of a lead wire for a feedthrough seal apparatus in accordance with at least one example of the invention.
Figure 14B:
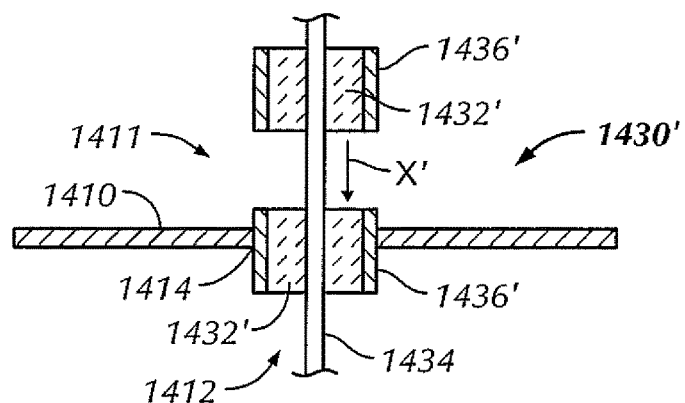
FIG. 14B is a cross-sectional view of a feedthrough seal apparatus in accordance with at least one example of the invention.
Figure 14C:
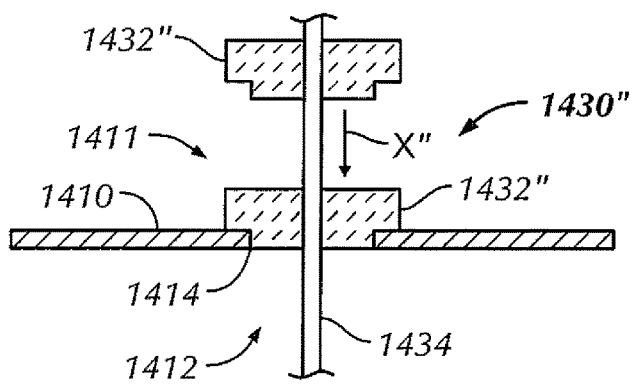
FIG. 14C is a cross-sectional view of a feedthrough seal apparatus in accordance with at least one example of the invention.

Referring to FIGS. 14A-14C, in some examples, a case 1410 (for instance, of a medical device or a component of a medical device) includes an opening 1414 with a lead wire 1434 extending from within an interior space 1412 of the case 1410 to an exterior 1411 of the case 1410. In various examples, a feedthrough seal apparatus 1430', 1430" can be used to seal the opening 1414 of the case while still allowing electrical communication between the interior space 1412 of the case 1410 and the exterior 1411 of the case 1410. In some examples, the feedthrough seal apparatus 1430', 1430" can be used to hermetically seal the opening 1414 of the case.

In some examples, referring specifically to FIG. 14B, the feedthrough seal apparatus 1430' includes a ferrule 1436' and a plug 1432' disposed at least partially within the ferrule 1436'. In various examples, in manners similar to those described herein, the plug 1432' can include a polymeric material, which can be affixed within the ferrule 1436' (for instance, with thermal joining, press-fitting, an adhesive, or the like or a combination thereof). The plug 1432' and the affixed ferrule 1436' can then be slid along the lead wire 1434 in the direction of arrow X' and into place within the opening 1414 of the case 1410. In some examples, the ferrule 1436' can then be engaged to the case 1410 within the opening 1414, for instance by welding or another engagement means. With the ferrule 1436' and the plug 1432' in place with respect to the lead wire 1434, in some examples, the plug 1432' can be affixed to the lead wire 1434 (for instance, with thermal joining, press-fitting, an adhesive, or the like or a combination thereof). In this way, the plug 1432' can be hermetically bonded to the ferrule 1436' and the lead wire 1434. In some examples, the feedthrough seal apparatus 1430' includes one or more of the following advantages:

(1) Relatively simple two/three-step process;
(2) Relatively inexpensive; and (3) Aids in locating the lead wire 1434 at the radial center of the opening 1414 in the case 1410.

In some examples, referring specifically to FIG. 14C, the feedthrough seal apparatus 1430" includes a plug 1432". That is, the feedthrough seal apparatus 1430" does not include a ferrule. In various examples, in manners similar to those described herein, the plug 1432" can include a polymeric material. The plug 1432" can be slid along the lead wire 1434 in the direction of arrow X" and into place within the opening 1414 of the case 1410. In some examples, the plug 1432" can then be engaged to the case 1410 within the opening 1414, for instance by thermal joining, an adhesive, or another engagement means. With the plug 1432" in place with respect to the lead wire 1434, in some examples, the plug 1432" can be affixed to the lead wire 1434 (for instance, with thermal joining, an adhesive, or the like or a combination thereof). In this way, in some examples, a one-component feedthrough seal apparatus 1430" can be used to seal the opening 1414 of the case 1410, thereby reducing, if not eliminating, the need for a ferrule. Furthermore, in some examples, the plug 1432" is hermetically bonded directly to the case 1410 and the lead wire 1434. In some examples, the feedthrough seal apparatus 1430" includes one or more of the following advantages:

(1) Relatively simple process (2) Less material cost (than a feedthrough seal apparatus with a ferrule)

(3) Aids in locating the lead wire 1434 at the radial center of the opening 1414 in the case 1410.

Figure 15:
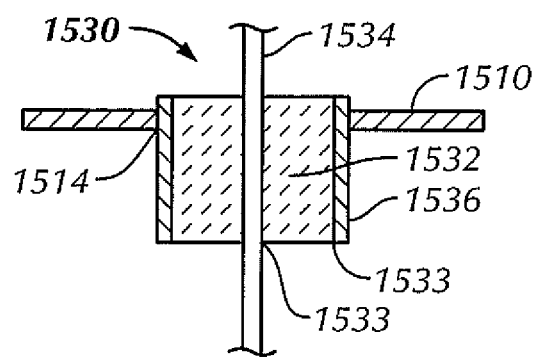
FIG. 15 is a cross-sectional view of a feedthrough seal apparatus in accordance with at least one example of the invention.

Referring to FIG. 15, in some examples, a feedthrough seal apparatus 1530 includes a ferrule 1536 engaged within an opening 1514 of a case 1510. As with previous examples, the ferrule 1536 can be engaged to the case 1510 by welding or another engagement means. In some examples, a plug 1532 is included at least partially within the ferrule 1536, the plug 1532 being affixed to the ferrule 1536. In some examples, the plug 1532 can include a thermoplastic polymeric material, such that, when heated (either bulk or locally, for instance), at least a portion 1533 of the plug 1532 abutting the ferrule 1536 melts or otherwise becomes flowable to interact with the ferrule 1536 and, with solidifying or hardening of the portion 1533, thermally join or otherwise affix the plug 1532 to the ferrule 1536. In like manner, in some examples, the plug 1532 can be heated (either bulk or locally, for instance) to melt at least a portion 1533 of the plug 1532 abutting a lead wire 1534 to interact with the lead wire 1534 and, with solidifying or hardening of the portion 1533, thermally join or otherwise affix the plug 1532 to the lead wire 1534. Although the ferrule 1536 is shown with straight walls in the present example, it should be understood that the ferrule 1536 can include a stepped portion or a tapered portion at an inner end, as described with respect to other examples herein, and/or a flange at an outer end, as is also described with respect to other examples herein.

Figure 16:
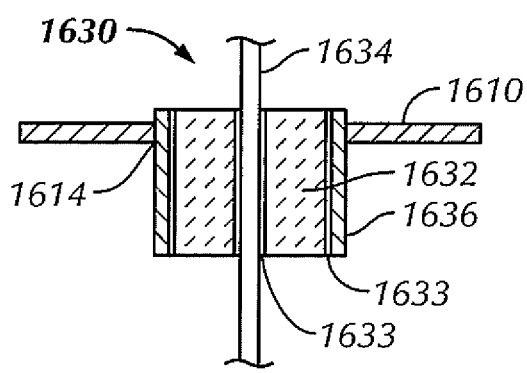
FIG. 16 is a cross-sectional view of a feedthrough seal apparatus in accordance with at least one example of the invention.

Referring to FIG. 16, in some examples, a feedthrough seal apparatus 1630 includes a ferrule 1636 engaged within an opening 1614 of a case 1610. As with previous examples, the ferrule 1636 can be engaged to the case 1610 by welding or another engagement means. In some examples, a plug 1632 is included at least partially within the ferrule 1636, the plug 1632 being affixed to the ferrule 1636. In some examples, the plug 1632 can be affixed to the ferrule 1636 using adhesive 1633 between the plug 1632 and the ferrule 1636, which, with solidifying, curing, or hardening of the adhesive 1633, affixes the plug 1632 to the ferrule 1636. In like manner, in some examples, the plug 1632 can be affixed to a lead wire 1634 using adhesive 1633 between the plug 1632 and the lead wire 1634, which, with solidifying, curing, or hardening of the adhesive 1633, affixes the plug 1632 to the lead wire 1634. Although the ferrule 1636 is shown with a stepped portion at an inner end in the present example, it should be understood that the ferrule 1636 can include straight walls or a tapered portion at an inner end, as described with respect to other examples herein, and/or a flange at an outer end, as is also described with respect to other examples herein. In some examples, the shape of the ferrule 1636 allows for relatively efficient seal formation. In some examples, the shape of the ferrule 1636 facilitates the accurate positioning of the plug 1632 and inhibits the plug 1632 from sliding toward the interior of the case 1610 within the ferrule 1636.

Referring to FIGS. 17A-17D, in some examples, a feedthrough seal apparatus 1730, 1730' includes a ferrule 1736, 1736' engaged within an opening 1714, 1714' of a case 1710, 1710'. As with previous examples, the ferrule 1736, 1736' can be engaged to the case 1710, 1710' by welding or another engagement means. In some examples, a plug 1732, 1732' is included at least partially within the ferrule 1736, 1736', the plug 1732, 1732' being affixed to the ferrule 1736, 1736'.

Figure 17A:
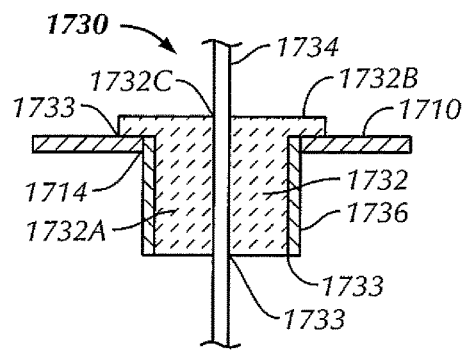
FIG. 17A is a cross-sectional view of a feedthrough seal apparatus in accordance with at least one example of the invention.

In some examples, referring to FIG. 17A, the plug 1732 can include a thermoplastic polymeric material, such that, when heated (either bulk or locally, for instance), at least a portion 1733 of the plug 1732 abutting the ferrule 1736 and/or case 1710 melts or otherwise becomes flowable to interact with the ferrule 1736 and/or the case 1710 and, with solidifying or hardening of the portion 1733, thermally join or otherwise affix the plug 1732 to the ferrule 1736 and/or the case 1710. In like manner, in some examples, the plug 1732 can be heated (either bulk or locally, for instance) to melt at least a portion 1733 of a longitudinal passage 1732C of the plug 1732 abutting a lead wire 1734 to interact with the lead wire 1734 and, with solidifying or hardening of the portion 1733, thermally join or otherwise affix the plug 1732 to the lead wire 1734. Although the ferrule 1736 is shown with straight walls in the present example, it should be understood that the ferrule 1736 can include a stepped portion or a tapered portion at an inner end, as described with respect to other examples herein, and/or a flange at an outer end, as is also described with respect to other examples herein.

Figure 17B:
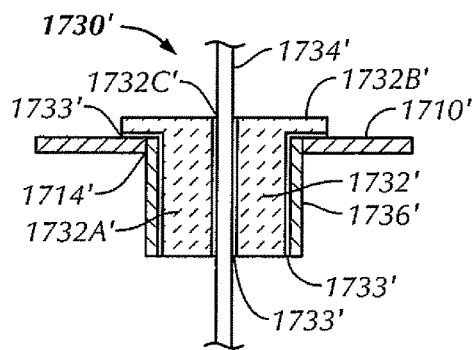
FIG. 17B is a cross-sectional view of a feedthrough seal apparatus in accordance with at least one example of the invention.
Figure 17C:
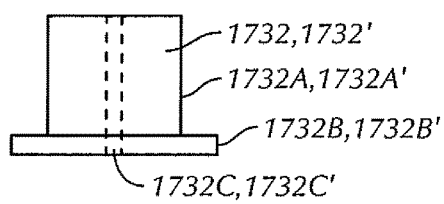
FIG. 17C is an end view of a plug of a feedthrough seal apparatus in accordance with at least one example of the invention.
Figure 17D:
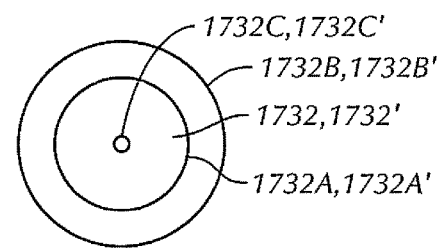
FIG. 17D is a side view of a plug of a feedthrough seal apparatus in accordance with at least one example of the invention.

Referring to FIG. 17B, in some examples, the plug 1732' can be affixed to the ferrule 1736' using adhesive 1733' between the plug 1732' and the ferrule 1736' and/or the case 1710', which, with solidifying, curing, or hardening of the adhesive 1733', affixes the plug 1732' to the ferrule 1736' and/or the case 1710'. In like manner, in some examples, the plug 1732' can be affixed to a lead wire 1734' using adhesive 1733' between a longitudinal passage 1732C' of the plug 1732' and the lead wire 1734', which, with solidifying, curing, or hardening of the adhesive 1733', affixes the plug 1732' to the lead wire 1734'. Although the ferrule 1736' is shown with straight walls in the present example, it should be understood that the ferrule 1736' can include a stepped portion or a tapered portion at an inner end, as described with respect to other examples herein, and/or a flange at an outer end, as is also described with respect to other examples herein.

Referring to FIGS. 17A-17D, the plug 1732, 1732', in some examples, includes a body portion 1732A, 1732A' configured to be inserted within the ferrule 1736, 1736' and a flange portion 1732B, 1732B' configured to remain outside the ferrule 1736, 1736' to abut a top of the ferrule 1736, 1736' and/or the case 1710, 1710'. The flange portion 1732B, 1732B' allows for increased contact area between the plug 1732, 1732' and the ferrule 1736, 1736' and/or the case 1710, 1710' than a plug having only the body portion to allow for increased affixation between the plug 1732, 1732' and the ferrule 1736, 1736' and/or the case 1710, 1710' either through thermal joining of the portion 1733 of the plug 1732 or by solidifying, curing, or hardening of the adhesive 1733'.

Figure 18:
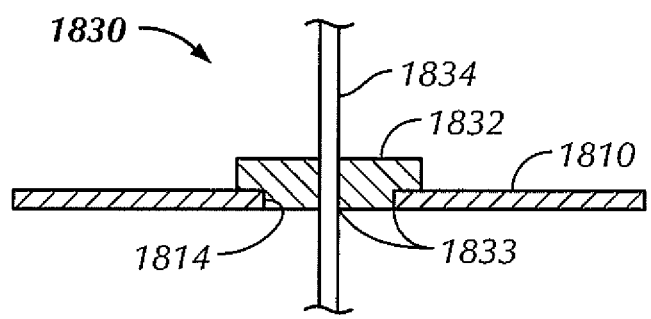
FIG. 18 is a cross-sectional view of a feedthrough seal apparatus in accordance with at least one example of the invention.

Referring to FIG. 18, in some examples, a feedthrough seal apparatus 1830 includes a plug 1832 engaged within an opening 1814 of a case 1810. In this way, in some examples, a one-component feedthrough seal apparatus 1830 can be used to seal the opening 1814 of the case 1810, thereby reducing, if not eliminating, the need for a ferrule. In some examples, the plug 1832 can include a thermoplastic polymeric material, such that, when heated (for instance, either bulk or locally), at least a portion 1833 of the plug 1832 abutting the case 1810 melts or otherwise becomes flowable to interact with the case 1810 and, with solidifying or hardening of the portion 1833, thermally join or otherwise affix the plug 1832 to the case 1810. In like manner, in some examples, the plug 1832 can be heated (for instance, either bulk or locally) to melt a portion 1833 of the plug 1832 abutting a lead wire 1834 to interact with the lead wire 1834 and, with solidifying or hardening of the portion 1833, thermally join or otherwise affix the plug 1832 to the lead wire 1834. In the example of FIG. 18, the feedthrough seal apparatus 1830 is substantially disk-shaped and is relatively thin. Depending upon the application, the environment, and other factors of the feedthrough seal apparatus 1830, other shapes of the feedthrough seal apparatus 1830 can be used in other examples, including, but not limited to, the shapes of the feedthrough seal apparatus examples described herein.

Figure 19:
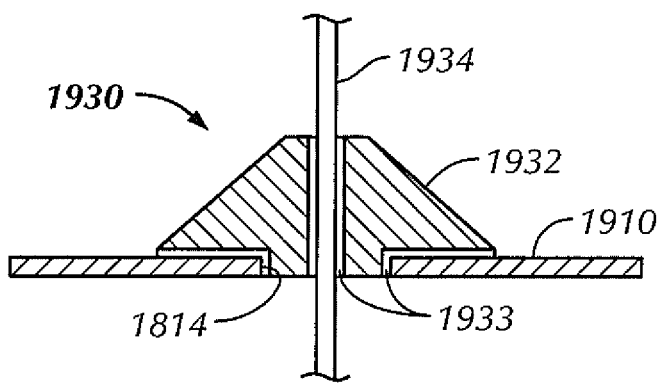
FIG. 19 is a cross-sectional view of a feedthrough seal apparatus in accordance with at least one example of the invention.
Figure 20A:
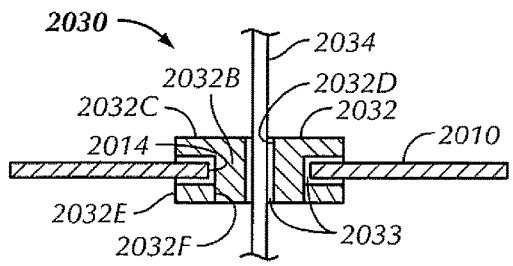
FIG. 20A is a cross-sectional view of a feedthrough seal apparatus in accordance with at least one example of the invention.
Figure 20B:
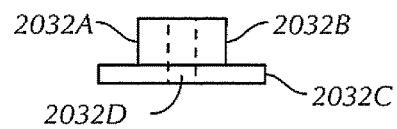
FIG. 20B is a side view of a first portion of a plug of a feedthrough seal apparatus in accordance with at least one example of the invention.
Figure 20C:
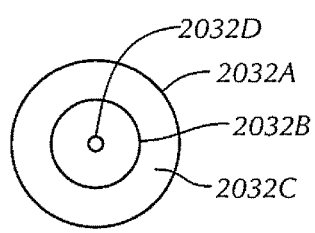
FIG. 20C is an end view of a first portion of a plug of a feedthrough seal apparatus in accordance with at least one example of the invention.
Figure 20D:
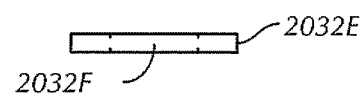
FIG. 20D is a side view of a second portion of a plug of a feedthrough seal apparatus in accordance with at least one example of the invention.
Figure 20E:
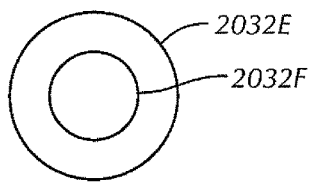
FIG. 20E is an end view of a second portion of a plug of a feedthrough seal apparatus in accordance with at least one example of the invention.

Referring to FIG. 19, in some examples, a feedthrough seal apparatus 1930 includes a plug 1932 engaged within an opening 1914 of a case 1910. In this way, in some examples, a one-component feedthrough seal apparatus 1930 can be used to seal the opening 1914 of the case 1910, thereby reducing, if not eliminating, the need for a ferrule. In some examples, the plug 1932 can include a polymeric material, which is then affixed within the opening 1914 of the case 1910. In some examples, the plug 1932 can be affixed to the case 1910 using adhesive 1933 between the plug 1932 and the case 1910, which, with solidifying, curing, or hardening of the adhesive 1933, affixes the plug 1932 to the case 1910. In like manner, in some examples, the plug 1932 can be affixed to a lead wire 1934 using adhesive 1933 between the plug 1932 and the lead wire 1934, which, with solidifying, curing, or hardening of the adhesive 1933, affixes the plug 1932 to the lead wire 1934. In the example of FIG. 19, the feedthrough seal apparatus 1930 is substantially frustoconically-shaped to increase contact area between the plug 1932 and at least one of the case 1910 and the lead wire 1934 than other differently-shaped feedthrough seal apparatuses, such as, for instance, the substantially disk-shaped plug 1932 of the feedthrough seal apparatus 1930 described above. In some examples, the plug 1932 is designed to maximize the area of contact with the case 1910 and the lead wire 1934. Depending upon the application, the environment, and other factors of the feedthrough seal apparatus 1930, other shapes of the feedthrough seal apparatus 1930 can be used in other examples, including, but not limited to, the shapes of the feedthrough seal apparatus examples described herein. In some examples, the shape of the plug 1932 allows for efficient seal formation. In some examples, the shape of the plug 1932 results in increased area of contact between the metal of the case 1910 and/or the lead wire 1934 and the polymeric material of the plug 1932.

Referring to FIGS. 20A-20E, in some examples, a feedthrough seal apparatus 2030 includes a plug 2032 engaged within an opening 2014 of a case 2010. In some examples, the plug 2032 includes a first portion 2032A and a second portion 2032E. In this way, in some examples, a two-component feedthrough seal apparatus 2030 can be used to seal the opening 2014 of the case 2010, thereby reducing, if not eliminating, the need for a ferrule. In some examples, the first and second portions 2032A, 2032E of the plug 2032 can include a polymeric material.

In some examples, the first portion 2032A of the plug 2032 includes a body portion 2032B configured to be inserted within the opening 2014 of the case 2010 and a flange portion 2032C configured to remain outside the opening 2014 to abut a top of the case 2010. The second portion 2032E, in some examples, includes an opening 2032F through the second portion 2032E, such that the second portion 2032E forms a substantially annular shape. In some examples, the opening 2032F of the second portion 2032E is sized to accept the body portion 2032B within the opening 2032F to enable the first portion 2032A and the second portion 2032E to be fitted together to form the plug 2032. In some examples, the second portion 2032E is configured to engage with the first portion 2032A. For instance, in some examples, the second portion 2032E is sized to frictionally engage with the first portion 2032A. In other examples, the second portion 2032E is configured to be threadably engaged with the first portion 2032A. In still other examples, the first portion 2032A and the second portion 2032E are configured to be fastened together, for instance, using adhesive.

In some examples, the first and second portions 2032A, 2032E of the plug 2032 are affixed within and around the opening 2014 of the case 2010. In some examples, the first portion 2032A of the plug 2032 is affixed to the case 2010 and within the opening 2014 using adhesive 2033 between the first portion 2032A of the plug 2032 and the case 2010, which, with solidifying, curing, or hardening of the adhesive 2033, affixes the first portion 2032A of the plug 2032 to the case 2010 within the opening 2014. The second portion 2032E of the plug 2032 can then be engaged with the first portion 2032A of the plug 2032 to essentially sandwich a portion of the case 2010 around the opening 2014 between the flange portion 2032C of the first portion 2032A and the second portion 2032E. In some examples, the second portion 2032E of the plug 2032 is affixed to the case 2010 using adhesive 2033 between the second portion 2032E of the plug 2032 and the case 2010, which, with solidifying, curing, or hardening of the adhesive 2033, affixes the second portion 2032E of the plug 2032 to the case 2010. In like manner, in some examples, the first portion 2032A of the plug 2032 can be affixed to a lead wire 2034 using adhesive 2033 between a longitudinal passage 2032D of the first portion 2032A of the plug 2032 and the lead wire 2034, which, with solidifying, curing, or hardening of the adhesive 2033, affixes the first portion 2032A of the plug 2032 to the lead wire 2034. Although described as being affixed to the case 2010 with adhesive 2033, in other examples, the plug 2032 can include a thermoplastic polymeric material, such that, when heated (for instance, either bulk or locally), at least a portion of the plug 2032 abutting the case 2010 melts or otherwise becomes flowable to interact with the case 2010 and, with solidifying or hardening of the portion, thermally join or otherwise affix the plug 2032 to the case 2010 and the lead wire 2034.

Referring to FIGS. 18-20A, in some examples, the case 1810, 1910, 2010 (for instance, proximate the opening 1814, 1914, 2014) can include one or more adhesion features to improve bonding, adhesion, and/or interaction between the case 1810, 1910, 2010 and the plug 1812, 1912, 2012. In some examples, such adhesion features can include, but are not limited to, surface roughness, bumps, ridges, dimples, channels, or other patterns or textures or a combination of patterns or textures. In similar manner to the various adhesion features described above with respect to the various ferrule examples and/or the various lead wire examples, employing one or more of such adhesion features with respect to the case 1810, 1910, 2010 can provide increased surface area and/or texture around and within which adhesive or polymeric material of the plug 1812, 1912, 2012 can form in order to enhance affixation of the plug 1812, 1912, 2012 to the case 1810, 1910, 2010. Although mentioned specifically with respect to the examples in FIGS. 18-20A, in various examples, it is noted that one or more of such adhesion features can be employed with respect to any of the examples of cases described herein in order to enhance adhesion, bonding, or interaction between the various plug examples and the various case examples described herein.

Various examples of feedthrough seal apparatuses are summarized in Table 1, below.

212, 1412. In some examples, the case 110, 210, 510, 1410, 1510, 1610, 1710, 1710', 1810, 1910, 2010 includes the opening 114, 214, 514, 1414, 1514, 1614, 1714, 1714', 1814, 1914, 2014 therein to allow access to the interior space 112, 212, 1412 from an exterior 111, 211, 1411 of the case 110, 210, 510, 1410, 1510, 1610, 1710, 1710', 1810, 1910, 2010. The method, in some examples, includes positioning a plug 132, 232, 332, 432, 932, 1032, 1132, 1232, 1332, 1332', 1332", 1432', 1432", 1532, 1632, 1732, 1732', 1832, 1932, 2032 within the opening 114, 214, 514, 1414, 1514, 1614, 1714, 1714', 1814, 1914, 2014 of the case 110, 210, 510, 1410, 1510, 1610, 1710, 1710', 1810, 1910, 2010. In some examples, a lead wire 134, 234, 334, 434, 934, 1034, 1134, 1234, 1334, 1334', 1334", 1434, 1534, 1634, 1734, 1734', 1834, 1934, 2034 is positioned within the opening 114, 214, 514, 1414, 1514, 1614, 1714, 1714', 1814, 1914, 2014. In some examples, the lead wire 134, 234, 334, 434, 934, 1034, 1134, 1234, 1334, 1334', 1334", 1434, 1534, 1634, 1734, 1734', 1834, 1934, 2034 includes a first end 134A and a second end 134B. In some examples, the lead wire 134, 234, 334, 434, 934, 1034, 1134, 1234, 1334, 1334', 1334", 1434, 1534, 1634, 1734, 1734', 1834, 1934, 2034 extends through the plug 132, 232, 332, 432, 932, 1032, 1132, 1232, 1332, 1332', 1332", 1432', 1432", 1532, 1632, 1732, 1732', 1832, 1932, 2032, such that the first end 134A of the lead wire 134,

TABLE 1

| Ferrule | Material | Method | Wire Design Surface | Wire Design Geometry | Ferrule Design Inner Surface | Ferrule Design Inside End | Ferrule Design Outside End |
|---|---|---|---|---|---|---|---|
| Yes | Polymer (filled or unfilled) | Press-Fit | Plain | Straight | Plain | Straight, Tapered or Stepped | Flange or No Flange |
|  |  | Thermally Joined Bulk (oven) | Featured, Perforated, or Plain | Straight or Bent (Helical) | Plain or Featured | Straight, Tapered or Stepped | Flange or No Flange |
|  |  | Local (laser, electrically) | Featured, Perforated, or Plain | Straight | Plain or Featured | Straight, Tapered or Stepped | Flange or No Flange |
|  |  | Adhesively Joined | Featured, Perforated, or Plain | Straight or Bent (Helical) | Plain or Featured | Straight, Tapered or Stepped | Flange or No Flange |
|  | Adhesive | Thermally Cured | Featured, Perforated, or Plain | Straight or Bent (Helical) | Plain or Featured | Tapered or Stepped | Flange or No Flange |
|  |  |  | Featured, Perforated, or Plain | Straight or Bent (Helical) | Plain or Featured | Tapered or Stepped | Flange or No Flange |
| No | Polymer (filled or unfilled) | Thermally Joined Bulk (oven) | Featured, Perforated, or Plain | Straight or Bent (Helical) | Not Applicable |  |  |
|  |  | Local (laser, electrically) | Featured, Perforated, or Plain | Straight |  |  |  |
|  |  | Adhesively Joined | Featured, Perforated, or Plain | Straight or Bent (Helical) |  |  |  |

In various examples, with reference to FIGS. 1-20E and the description herein, a method is included for making a feedthrough seal apparatus 130, 230, 330, 430, 1230, 1330, 1330', 1330", 1430', 1430", 1530, 1630, 1730, 1730', 1830, 1930, 2030. In some examples, the feedthrough seal apparatus 130, 230, 330, 430, 1230, 1330, 1330', 1330", 1430', 1430", 1530, 1630, 1730, 1730', 1830, 1930, 2030 is configured to seal an opening 114, 214, 514, 1414, 1514, 1614, 1714, 1714', 1814, 1914, 2014 in a device 100, the device 100 including a case 110, 210, 510, 1410, 1510, 1610, 1710, 1710', 1810, 1910, 2010 surrounding an interior space 112, 234, 334, 434, 934, 1034, 1134, 1234, 1334, 1334', 1334", 1434, 1534, 1634, 1734, 1734', 1834, 1934, 2034 is disposed within the interior space 112, 212, 1412 of the case 110, 210, 510, 1410, 1510, 1610, 1710, 1710', 1810, 1910, 2010 and the second end 134B extends from the plug 132, 232, 332, 432, 932, 1032, 1132, 1232, 1332, 1332', 1332", 1432', 1432", 1532, 1632, 1732, 1732', 1832, 1932, 2032 to the exterior 111, 211, 1411 of the case 110, 210, 510, 1410, 1510, 1610, 1710, 1710', 1810, 1910, 2010, wherein the lead wire 134, 234, 334, 434, 934, 1034, 1134, 1234, 1334, 1334', 1334", 1434, 1534, 1634, 1734, 1734', 1834, 1934, 2034 is configured to allow electrical communication between the interior space 112, 212, 1412 of the case 110, 210, 510, 1410, 1510, 1610, 1710, 1710', 1810, 1910, 2010 and the exterior 111, 211, 1411 of the case 110, 210, 510, 1410, 1510, 1610, 1710, 1710', 1810, 1910, 2010.

In some examples, the method further includes positioning a ferrule 236, 336, 436, 536, 636, 736, 836, 936, 1036, 1136, 1236, 1336, 1336', 1336", 1436', 1536, 1636, 1736, 1736' within the opening 114, 214, 514, 1414, 1514, 1614, 1714, 1714', 1814, 1914, 2014 of the case 110, 210, 510, 1410, 1510, 1610, 1710, 1710', 1810, 1910, 2010, wherein the plug 132, 232, 332, 432, 932, 1032, 1132, 1232, 1332, 1332', 1332", 1432', 1532, 1632, 1732, 1732' is positioned within the ferrule 236, 336, 436, 536, 636, 736, 836, 936, 1036, 1136, 1236, 1336, 1336', 1336", 1436', 1536, 1636, 1736, 1736'. In some examples, positioning the plug 132, 232, 332, 432, 932, 1032, 1132, 1332, 1332', 1332", 1432' includes inserting adhesive within the ferrule 236, 336, 436, 536, 636, 736, 836, 936, 1036, 1136, 1236, 1336, 1336', 1336", 1436', 1536, 1636, 1736, 1736' and around the lead wire 134, 234, 334, 434, 934, 1034, 1134, 1234, 1334, 1434, 1534, 1634. In this way, the plug 132, 232, 332, 432, 932, 1032, 1132, 1332, 1332', 1332", 1432' is formed at least partially, if not entirely, from adhesive.

In some examples, the plug 132, 232, 332, 432, 932, 1032, 1132, 1232, 1332, 1332', 1332", 1432', 1532, 1632, 1732, 1732' is formed at least partially, if not entirely, from one or more polymeric materials. In some examples, the plug 132, 232, 332, 432, 932, 1032, 1132, 1232, 1332, 1332', 1332", 1432', 1632, 1732' is affixed to the ferrule 236, 336, 436, 536, 636, 736, 836, 936, 1036, 1136, 1236, 1336, 1336', 1336", 1436', 1636, 1736' and the lead wire 134, 234, 334, 434, 934, 1034, 1134, 1234, 1334, 1334', 1334", 1434, 1634, 1734' using adhesive. In other examples, the plug 132, 232, 332, 432, 932, 1032, 1132, 1232, 1332, 1332', 1332", 1432', 1532, 1732 includes a thermoplastic polymeric material, wherein the plug 132, 232, 332, 432, 932, 1032, 1132, 1232, 1332, 1332', 1332", 1432', 1532, 1732 is thermally joined to the ferrule 236, 336, 436, 536, 636, 736, 836, 936, 1036, 1136, 1236, 1336, 1336', 1336", 1436', 1536, 1736 and the lead wire 134, 234, 334, 434, 934, 1034, 1134, 1234, 1334, 1334', 1334", 1434, 1534, 1734 by heating the plug 132, 232, 332, 432, 932, 1032, 1132, 1232, 1332, 1332', 1332", 1432', 1532, 1732. In some examples, the plug 132, 232, 332, 432, 1232, 1332, 1332', 1332", 1432' is affixed within the ferrule 236, 336, 436, 1236, 1336, 1336', 1336", 1436' and/or to the lead wire 134, 234, 334, 434, 1234, 1334, 1334', 1334", 1434 by press-fitting the plug 132, 232, 332, 432, 1232, 1332, 1332', 1332", 1432' at least partially within the ferrule 236, 336, 436, 1236, 1336, 1336', 1336", 1436' and/or around the lead wire 134, 234, 334, 434, 1234, 1334, 1334', 1334", 1434. In some examples, the ferrule 236, 536, 1436', 1536, 1636, 1736, 1736' is affixed within the opening 214, 514, 1414, 1514, 1614, 1714, 1714' by welding the ferrule 236, 536, 1436', 1536, 1636, 1736, 1736' to the ease 210, 510, 1410, 1510, 1610, 1710, 1710'.

In some examples, the plug 132, 1432", 1832, 1932, 2032 is affixed within the opening 114, 1414, 1814, 1914, 2014 of the case 110, 1410, 1810, 1910, 2010. That is, the feedthrough seal apparatus 130, 1430", 1830, 1930, 2030 includes no ferrule and the plug 132, 1432", 1832, 1932, 2032 is bonded directly to the case 110, 1410, 1810, 1910, 2010. In some examples, the plug 132, 1432", 1832, 1932, 2032 includes a polymeric material. In some examples, the plug 132, 1432", 1932, 2032 is affixed within the opening 114, 1414, 1914, 2014 of the case 110, 1410, 1910, 2010 and to the lead wire 134, 1434, 1934, 2034 using an adhesive. In some examples, the plug 132, 1432", 1832, 2032 includes a thermoplastic polymeric material, wherein the plug 132, 1432", 1832, 2032 is thermally joined to the case 110, 1410, 1810, 2010 and the lead wire 134, 1434, 1834, 2034 by heating the plug 132, 1432", 1832, 2032.

The present inventors have recognized various advantages of the subject matter described herein. For instance, in some examples, the present subject matter is advantageous for use in a feedthrough seal of a component of a medical device. In some examples, the present inventors have recognized that the present subject matter can be advantageous for use in feedthrough seals that are substantially functionally equivalent to, relatively simpler to manufacture than, and relatively less expensive than GTMS. For instance, compared to current seals (such as GTMS, for instance), the present subject matter, in various examples, can reduce manufacturing time, manufacturing difficulty, and material cost while achieving a seal that can withstand voltages of the component, inhibit current leakages between the wire and case, physically inhibit the wire and case from contacting one another, and inhibit movement of electrolyte molecules outside of the component. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses, systems, and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising"

are open-ended, that is, an apparatus, system, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A feedthrough seal apparatus for a device, the device including a case surrounding an interior space, the case including an opening therein to allow access to the interior space from an exterior of the case, the feedthrough seal apparatus comprising:
a plug disposed within the opening of the case, wherein the plug is formed from at least one of a polymeric material and an adhesive material; and
a lead wire including a first end and a second end, the lead wire in direct contact with and extending through the plug, such that the first end of the lead wire is disposed within the interior space of the case and the second end extends from the plug to the exterior of the case, the lead wire including a first adhesion feature disposed on a portion of the lead wire in direct contact with the plug, the first adhesion feature being configured to increase adhesion between the lead wire and the plug, wherein the first adhesion feature includes one or more of a bent portion of the lead wire, a textured surface, and a porous surface, wherein the lead wire is configured to allow electrical communication between the interior space of the case and the exterior of the case, and wherein the feedthrough seal apparatus is configured to seal the opening in the case, the plug being configured to electrically insulate the lead wire from the case.

2. The feedthrough seal apparatus of claim 1, comprising a ferrule attached to the case and disposed within the opening, wherein the plug is affixed within the ferrule.

3. The feedthrough seal apparatus of claim 2, wherein the plug is formed entirely from the polymeric material.

4. The feedthrough seal apparatus of claim 3, wherein the polymeric material of the plug includes a thermoplastic polymeric material configured to be thermally joined to the ferrule with heating of the thermoplastic polymeric material, thereby affixing the plug to the ferrule.

5. The feedthrough seal apparatus of claim 3, wherein the plug is sized and shaped to correspond to an interior of the ferrule, the plug being press-fit into the ferrule to affix the plug at least partially within the ferrule.

6. The feedthrough seal apparatus of claim 2, wherein the ferrule includes a second adhesion feature configured to increase adhesion between the ferrule and the plug.

7. The feedthrough seal apparatus of claim 2, wherein the ferrule includes an inwardly-extending portion, the inwardly-extending portion extending from a sidewall of the ferrule toward an interior of the ferrule.

8. The feedthrough seal apparatus of claim 7, wherein the inwardly-extending portion includes a stepped feature.

9. The feedthrough seal apparatus of claim 7, wherein the inwardly-extending portion includes a tapered feature.

10. The feedthrough seal apparatus of claim 2, wherein the plug is formed entirely from the adhesive material.

11. The feedthrough seal apparatus of claim 10, wherein the adhesive material of the plug includes epoxy.

12. The feedthrough seal apparatus of claim 2, wherein the plug is formed from both the adhesive material and the polymeric material.

13. The feedthrough seal apparatus of claim 1, wherein the plug is formed entirely from the polymeric material, the plug being affixed directly to the case within the opening.

14. The feedthrough seal apparatus of claim 1, wherein the textured surface of the first adhesion feature includes a plurality of dimples within the lead wire within which the at least one of the polymeric material and the adhesive material interacts to increase adhesion between the lead wire and the plug.

15. A feedthrough seal apparatus for a device, the device including a case surrounding an interior space, the case including an opening therein to allow access to the interior space from an exterior of the case, the feedthrough seal apparatus comprising:
a ferrule attached to the case and disposed within the opening;
a plug affixed within the ferrule, wherein the plug is formed from at least one of a polymeric material and an adhesive material; and
a lead wire including a first end and a second end, the lead wire in direct contact with and extending through the plug, such that the first end of the lead wire is disposed within the interior space of the case and the second end extends from the plug to the exterior of the case, the lead wire including a first adhesion feature disposed on a portion of the lead wire in direct contact with the plug, the first adhesion feature being configured to increase adhesion between the lead wire and the plug, wherein the first adhesion feature includes one or more of a bent portion of the lead wire, a textured surface, and a porous surface, wherein the lead wire is configured to allow electrical communication between the interior space of the case and the exterior of the case, and wherein the feedthrough seal apparatus is configured to seal the opening in the case, the plug being configured to electrically insulate the lead wire from the case.

16. The feedthrough seal apparatus of claim 15, wherein the textured surface of the first adhesion feature includes a plurality of dimples within the lead wire within which the at least one of the polymeric material and the adhesive material interacts to increase adhesion between the lead wire and the plug.

17. The feedthrough seal apparatus of claim 15, wherein the ferrule includes a second adhesion feature, the second adhesion feature of the ferrule including at least one of a textured surface and a porous surface.

18. The feedthrough seal apparatus of claim 15, wherein the ferrule includes an inwardly-extending portion, the inwardly-extending portion extending from a sidewall of the ferrule toward an interior of the ferrule, the inwardly-extending portion including at least one of a stepped feature and a tapered feature.

19. The feedthrough seal apparatus of claim 15, wherein the plug is formed from both the adhesive material and the polymeric material.

20. The feedthrough seal apparatus of claim 15, wherein the polymeric material of the plug includes a thermoplastic polymeric material configured to be thermally joined to the lead wire with heating of the thermoplastic polymeric material, thereby affixing the plug to the lead wire and the first adhesion feature of the lead wire.

* * * * *